United States Patent [19]

Bodor et al.

[11] 4,275,064
[45] * Jun. 23, 1981

[54] TRANSIENT PRO-DRUG FORMS OF XANTHINE DERIVATIVES AND THEIR USE AS TOPICAL ANTI-INFLAMMATORY AGENTS

[75] Inventors: Nicholas S. Bodor, Lawrence; Kenneth B. Sloan, Eudora, both of Kans.

[73] Assignee: INTERx Research Corporation, Lawrence, Kans.

[*] Notice: The portion of the term of this patent subsequent to Dec. 6, 1994, has been disclaimed.

[21] Appl. No.: 34,630

[22] Filed: Apr. 30, 1979

Related U.S. Application Data

[63] Continuation of Ser. No. 832,448, Sep. 12, 1977, abandoned, which is a continuation-in-part of Ser. No. 655,786, Feb. 6, 1976, Pat. No. 4,061,753.

[51] Int. Cl.³ ............... A61K 31/52; C07D 473/08
[52] U.S. Cl. ........................... 424/253; 542/420; 542/427; 544/118; 544/267; 544/270; 544/271; 544/272
[58] Field of Search ............ 544/267, 271, 272, 270; 542/427; 424/253

[56] References Cited

U.S. PATENT DOCUMENTS 3,029,239  4/1962  Kohlstaedt et al. ............ 544/272
4,061,753  12/1977  Bodor et al. .................... 424/253

FOREIGN PATENT DOCUMENTS 1265879  5/1961  France ........................... 544/267

OTHER PUBLICATIONS

Roth et al., *Chemical Abstracts*, 64:5093g.

*Primary Examiner*—Paul M. Coughlan, Jr.
*Attorney, Agent, or Firm*—Burns, Doane, Swecker & Mathis

[57] ABSTRACT

Compounds of the formula:

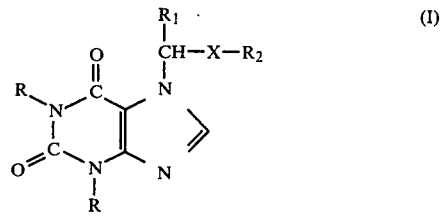

useful in treating dermal inflammation in warm-blooded animals are provided.

51 Claims, No Drawings

TRANSIENT PRO-DRUG FORMS OF XANTHINE DERIVATIVES AND THEIR USE AS TOPICAL ANTI-INFLAMMATORY AGENTS

CROSS-REFERENCE TO RELATED APPLICATIONS

This application is a continuation of application Ser. No. 832,448, filed Sept. 12, 1977 and now abandoned, which is a continuation-in-part application of our earlier co-pending application, Ser. No. 655,786, filed Feb. 6, 1976, now U.S. Pat. No. 4,061,753.

BACKGROUND OF THE INVENTION

1. Field of the Invention

The present invention is directed to novel transient pro-drugforms of certain xanthine derivatives, and more particularly, xanthine derivatives useful in the treatment of dermal inflammation.

For the purposes of this application, the term "pro-drug" denotes a derivative of a known and proven prior art xanthine compound (e.g., theophylline), which derivative, when administered topically to a warm-blooded animal, "cleaves" in such a manner as to release the proven drug form in the dermal tissue thereof.

The term "transient" denotes dermal enzymatic and/or chemical hydrolytic "cleaveage" of the compounds of the instant invention in such a manner that the proven drug form (parent xanthine compound, e.g., theophylline) is released and the remaining "cleaved" moiety remains nontoxic and metabolized in such a manner that nontoxic, metabolic products are produced.

2. Description of the Prior Art

The development of pro-drug forms of certain xanthine compounds such as theophylline was initially carried out in order that such compounds could be used in the treatment of psoriasis. The antipsoriatic use of the compounds of Formula (I) is diclosed and claimed in applicants' parent application, previously identified, the subject matter of which is incorporated herein by reference. Quite unexpectedly, it has now been determined that these compounds exhibit a dermal anti-inflammatory activity as well.

PRIOR ART RE: FORMULA (I)

Chemical Abstracts, 64:5093c-g(1966) discloses the 7-acetoxymethyl derivative of theophylline with no apparent utility whatsoever. Because this compound exhibits such a poor water/heptane partition coefficient (~7.5) as a 7-acloxymethyl ester of theophylline, it virtually cannot penetrate the dermal membrane. Thus, its usefulness as a dermal anti-inflammatory agent is nil.

A direct correlation between percutaneous absorption and partition coefficients of the absorbed compound is water and some lipid-like materials, e.g., oil, heptane octanol has been shown. See, M. Katz and Z. I. Shaiki, *J. Pharm. Sci.*, 54, 591 (1965) and J. E. Treherne, *J. Physiol.*, 133, 171 (1956). Normally, the closer this partition coefficient is to unity, the better the compound is absorbed, providing, however, the compound in question has appreciable solubility in both the water and lipid phase. However, if anything, the skin is more permeable to lipid soluble substances. See, J. H. Wills, "Percutaneous Absorption" in *Pharmacology and The Skin,* W. Montagny, E. J. Van Scott and R. B. Stoughton, Ed., Chapter XII, Appleton-Century Grofts, New York, New York, 1972, p. 172. Certain xanthine compounds, such as theophylline, on the other hand, are almost insoluble in lipid-like solvents (e.g., heptane). Consequently, their use in the topical treatment of inflammation has not heretofore been investigated. Moreover, the above criteria also makes it very clear that the target xanthine pro-drug compound employed should have an increased lipid solubility if it is to be absorbed percutaneously and reach the dermal site where therapeusis is required.

The remaining criteria for the target pro-drug is that it undergo rapid hydrolysis once it reaches its site of therapeutic activity. One group of candidate compounds which appears to meet the above criteria is the higher 7-acyloxymethyl derivatives of theophylline [encompassed by the compounds of Formula (I)]. Another group of candidate compounds [the compounds encompassed by Formula (I)] while not meeting this criteria, do, in fact, exhibit excellent penetration through the dermal membrane via a mechanism which has not yet been determined. As noted earlier, the 7-acetoxymethyl derivative whose water/heptane partition coefficient is 7.5 cannot penetrate the dermal membrane.

Since applicants' parent application was filed, it has beendemonstrated that the compound of Formula (I) possess yet another unexpected therapeutic activity, totally unrelated to the previously discovered antipsoriatic activity, namely, a dermal anti-inflammatory activity. That is, the compounds of Formula (I) have been found useful as general topical nonsteroidal anti-inflammatory agents useful in the relief of general topical anti-inflammatory conditions. This utility has not been attributed to the ability of these compounds to elevate cyclic AMP (Adenosine monophosphate). At present, their mechanism of action has not yet been determined.

SUMMARY OF THE INVENTION

It is one object of the present invention to provide novel, transient pro-drug forms of selected xanthine compounds (e.g., theophylline), which are extremely useful in the topical treatment of dermal inflammation in warm-blooded animals, e.g., humans.

It is another object of the present invention to provide novel, transient pro-drug forms of selected xanthine derivatives which, following topical administration to the skin of a warm-blooded animal will penetrate the dermal membrane and cleave in such a manner as to enable the original parent xanthine moiety (e.g., theophylline) to be released at its therapeutic dermal site of anti-inflammatory activity and to further permit the cleaved moiety(ies) unassociated with the parent xanthine moiety to be metabolized in a nontoxic fashion.

The foregoing objects are achieved by topically administering to a warm-blooded animal afflicted with dermal inflammation, an effective anti-inflammatory amount of a compound having the formula:

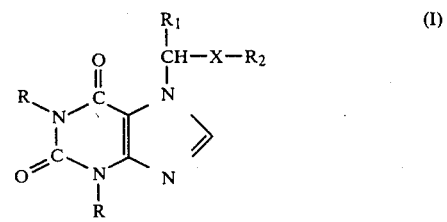

wherein R, which may be the same or different, represents a member selected from the group consisting of —CH$_3$, —C$_2$H$_5$, —C$_3$H$_7$, iso-C$_3$H$_7$, —C$_4$H$_9$, iso-C$_4$H$_9$, pentyl, benzyl, allyl, 2-hydroxyethyl, cyclohexyl, 2-isobutenyl, hydroxymethyl, 2-phenylethyl and —CH$_2$O—R$_2$, wherein R$_2$ is defined infra; wherein R$_1$ represents a member selected from the group consisting of H, C$_1$–C$_7$ straight or branched alkyl, CCl$_3$, CBr$_3$, CI$_3$,

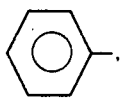

CH$_3$O—CH$_2$—, (CH$_3$)$_2$NCH$_2$—,

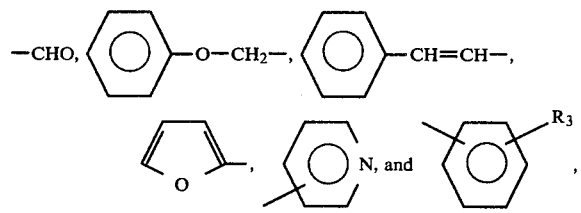

wherein R$_3$ represents a member selected from the group consisting of —OH, halogen,

—OCH$_3$,

—COOCH$_3$, —NO$_2$ and —OCOCH$_3$; wherein X is —O—, —S—, or

and wherein R$_2$ represents a member selected from the group consisting of

wherein R$_4$ is a member selected from the group consisting of C$_2$–C$_{20}$ straight or branched alkyl, cyclo(C$_3$–C$_{10}$)alkyl,

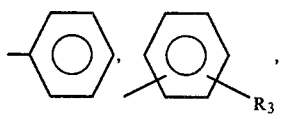

wherein R$_3$ is defined as above,

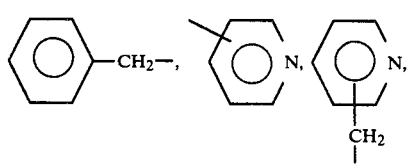

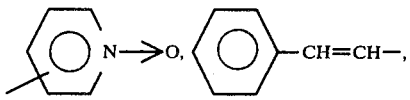

the residue of any naturally occurring amino acid, the residue of any N-substituted amino acid, wherein said substituent is any amino acid protective group cleavable via hydrogenolysis or hydrolysis, the residue of an N,N-C$_1$–C$_5$-dialkyl, cycloalkyl, N-heteroaromatic or N-C$_1$–C$_5$ alkyl aniline amino acid,

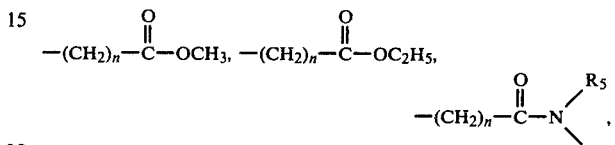

wherein n represents an integer of from 1–5 and R$_5$ and R$_6$ which may be the same or different represent C$_1$–C$_5$ alkyl or together form a heterocyclic ring with the N atom to which they are attached, imidazolyl, O—C$_1$–C$_8$ alkyl, O-benzyl, O-phenyl and

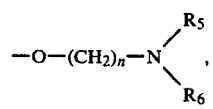

wherein n, R$_5$ and R$_6$ are defined as above; and wherein R$_2$ further represents a member selected from the group consisting of straight or branched C$_1$–C$_{20}$ alkyl,

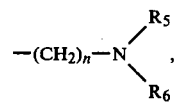

wherein n, R$_5$ and R$_6$ are defined as above, phenyl, tolyl, xylyl, and —SO$_2$—R$_7$, wherein R$_7$ is a straight or branched C$_1$–C$_{20}$ alkyl useful in treating dermal inflammation in warm-blooded animals are provided.

In reference to Formula (I), the term "halogen" denotes Cl, Br, I; the term C$_2$–C$_{20}$ straight or branched alkyl in relation to substituent "R$_4$" carries a preferred range of C$_3$–C$_7$; the phrase "amino acid protective group cleavable via hydrogenolysis or hydrolysis" in relation to substituent "R$_4$" denotes any such member, e.g., formyl, benzyloxy, carbonyl, t-butyloxycarbonyl, etc.; and the phrase "or together form a heterocyclic ring with the N atom to which they are attached" denotes any suitable ring such as pyrrolidone, piperidine, morpholine, piperazine, imidazoline, thiazolidine, isoxazolidine, etc.; and "N-heteroaromatic" denotes any N-heteromatic ring, wherein the N atom is freely substitutable (e.g., imidazole, benzimidazole, pyrazole, thiazole, pyrole, isoxazine, etc.)

As used herein, the term "naturally occurring amino acid" includes without limitation:
Glycine
Alanine
Valine
Leucine
Isoleucine Cysteine
Crystine
Methionine
Serine
Threonine
Aspartic acid
Glutamic acid
Arginine
Lysine
Hydroxylsine
Phenylalanine
Tyrosine
Asparagine
Glutamine
Proline
Hydroxyproline
Histidine
Tryptophan
Pyroglutamic acid Similarly, the import of the phrase "amino acid protective group 'cleavable' via hydrogenolysis or hydrolysis" can be further gained from a review of U.S. Pat. No. 3,803,120—Felix.

DETAILED DESCRIPTION OF THE INVENTION

While all the compounds encompassed within the above-described generic formula satisfy the objectives of the instant invention, nevertheless, certain selected compounds, as set out below, remain preferred:

(1) 7-Ethoxymethyl-theophylline
(2) 7-Propyloxymethyl-theophylline
(3) 7-Butyloxymethyl-theophylline
(4) 7-Benzyloxymethyl-theophylline
(5) 7-(1-Pyridyl)methyl-theophylline chloride
(6) 7-(N,N-dimethylaminoethyloxy)methyl-theophylline
(7) 7-Acetyloxymethyl-theophylline
(8) 7-Propionyloxymethyl-theophylline
(9) 7-Butanoyloxymethyl-theophylline
(10) 7-Pivalyloxymethyl-theophylline
(11) 7-Hexanoyloxymethyl-theophylline
(12) 7-Heptanoyloxymethyl-theophylline
(13) 7-Octanoyloxymethyl-theophylline
(14) 7-Ethoxycarbonyloxymethyl-theophylline
(15) 7-Benzyloxycarbonyloxymethyl-theophylline
(16) 7-(2',2',2'-Trichloroethyloxycarbonyloxymethyl)-theophylline
(17) 7-(N,N-Dimethylglycyloxymethyl)-theophylline
(18) 7-(1-Piperidylacetyloxymethyl)-theophylline
(19) 7-Benzoyloxymethyl-theophylline
(20) 7-p-Toluyloxymethyl-theophylline
(21) 7-Phenylacetyloxymethyl-theophylline
(22) 7-Picolinoyloxymethyl-theophylline
(23) 7-Nicotinoyloxymethyl-theophylline
(24) 7-N-Formylglycyloxymethyl-theophylline
(25) 7-Glycyloxymethyl-theophylline
(26) 7-Cinnamoyloxymethyl-theophylline
(27) 7-N-Benzyloxycarbonylglycyloxymethyl-theophylline
(28) 7-Methylsuccinyloxymethyl-theophylline
(29) 7-(N,N-Dimethylsuccinamyloxymethyl)-theophylline
(30) 7-(N,N-Diethylsuccinamyloxymethyl)-theophylline
(31) 7-(N,N,N-Trimethylglycyloxymethyl)-theophylline chloride
(32) 7-(N,N,N-Triethylglycyloxymethyl)-theophylline chloride
(33) 7-(α-Ethoxyethyl)-theophylline
(34) 7-(α-Benzyloxyethyl)-theophylline
(35) 7-(α-Acetyloxyethyl)-theophylline
(36) 7-(α-Propionyloxyethyl)-theophylline
(37) 7-(α-Butanoyloxyethyl)-theophylline
(38) 7-(α-Pivalyloxyethyl)-theophylline
(39) 7-(α-Hexanoyloxyethyl)-theophylline
(40) 7-(α-Octanoyloxyethyl)-theophylline
(41) 7-(αEthoxycarbonyloxyethyl)-theophylline
(42) 7-[α-(N,N-Dimethylglycyloxy)ethyl]-theophylline
(43) 7-[α-(1-Piperidylacetyloxy)ethyl]-theophylline
(44) 7-(α-Benzoyloxyethyl)-theophylline
(45) 7-(α-Picolinoyloxyethyl)-theophylline
(46) 7-[α-(N-Formylglycyloxy)ethyl]-theophylline
(47) 7-[α-(N-Benzyloxycarbonylglycyloxy)ethyl]-theophylline
(48) 7-(α-Methylsuccinyloxyethyl)-theophylline
(49) 7-[α-(N,N-Dimethylsuccinamyloxy)ethyl]-theophylline
(50) 7-[α-(N,N,N-Trimethylglycyloxy)ethyl]-theophylline chloride
(51) 7-(α-Ethoxybenzyl)-theophylline
(52) 7-(α-Benzyloxybenzyl)-theophylline
(53) 7-(α-Acetyloxybenzyl)-theophylline
(54) 7-(α-Propionyloxybenzyl)-theophylline
(55) 7-(α-Butanoyloxybenzyl)-theophylline
(56) 7-(α-Pivalyloxybenzyl)-theophylline
(57) 7-(α-Hexanoyloxybenzyl)-theophylline
(58) 7-(α-Octanoyloxybenzyl)-theophylline
(59) 7-(α-Ethoxycarbonyloxybenzyl)-theophylline
(60) 7-[α-(N,N-Dimethylglycyloxy)benzyl]-theophylline
(61) 7-[α-(1-Piperidylacetyloxy)benzyl]-theophylline
(62) 7-(α-Benzoyloxybenzyl)-theophylline
(63) 7-(α-Picolinoyloxybenzyl)-theophylline
(64) 7-[α-(N-Formylglycyloxy)benzyl]-theophylline
(65) 7-[α-(N-Benzyloxycarbonylglycyloxy)benzyl]-theophylline
(66) 7-(α-Methylsuccinyloxybenzyl)-theophylline
(67) 7-[α-(N,N-Dimethylsuccinamyloxy)benzyl]-theophylline
(68) 7-[α-(N,N,N-Trimethylglycyloxy)benzyl]-theophylline chloride
(69) 7-Ethoxymethyl-1-methyl-3-isobutylxanthine
(70) 7-Propyloxymethyl-1-methyl-3-isobutylxanthine
(71) 7-Butyloxymethyl-1-methyl-3-isobutylxanthine
(72) 7-Benzyloxymethyl-1-methyl-3-isobutylxanthine
(73) 7-(1-Pyridyl)methyl-1-methyl-3-isobutylxanthine chloride
(74) 7-(N,N-dimethylaminoethyloxy)methyl-1-methyl-3-isobutylxanthine
(75) 7-Acetyloxymethyl-1-methyl-3-isobutylxanthine
(76) 7-Propionyloxymethyl-1-methyl-3-isobutylxanthine
(77) 7-Butanoyloxymethyl-1-methyl-3-isobutylxanthine
(78) 7-Pivalyloxymethyl-1-methyl-3-isobutylxanthine
(79) 7-Hexanoyloxymethyl-1-methyl-3-isobutylxanthine
(80) 7-Heptanoyloxymethyl-1-methyl-3-isobutylxanthine
(81) 7-Octanoyloxymethyl-1-methyl-3-isobutylxanthine
(82) 7-Ethoxycarbonyloxymethyl-1-methyl-3-isobutylxanthine
(83) 7-Benzyloxycarbonyloxymethyl-1-methyl-3-isobutylxanthine
(84) 7-(2',2',2'-Trichloroethyloxycarbonyloxymethyl)-1-methyl-3-isobutylxanthine

(85) 7-(N,N-Dimethylglycyloxymethyl)-1-methyl-3-isobutylxanthine
(86) 7-(1-Piperidylacetyloxymethyl)-1-methyl-3-isobutylxanthine
(87) 7-Benzoyloxymethyl-1-methyl-3-isobutylxanthine
(88) 7-p-Toluyloxymethyl-1-methyl-3-isobutylxanthine
(89) 7-Phenylacetyloxymethyl-1-methyl-3-isobutylxanthine
(90) 7-Picolinoyloxymethyl-1-methyl-3-isobutylxanthine
(91) 7-Nicotinoyloxymethyl-1-methyl-3-isobutylxanthine
(92) 7-N-Formylglycyloxymethyl-1-methyl-3-isobutylxanthine
(93) 7-Glycyloxymethyl-1-methyl-3-isobutylxanthine
(94) 7-Cinnamoyloxymethyl-1-methyl-3-isobutylxanthine
(95) 7-N-Benzyloxycarbonylglycyloxymethyl-1-methyl-3-isobutylxanthine
(96) 7-Methylsuccinyloxymethyl-1-methyl-3-isobutylxanthine
(97) 7-(N,N-Dimethylsuccinamyloxymethyl)-1-methyl-3-isobutylxanthine
(98) 7-(N,N-Diethylsuccinamyloxymethyl)-1-methyl-3-isobutylxanthine
(99) 7-(N,N,N-Trimethylglycyloxymethyl)-1-methyl-3-isobutylxanthine chloride
(100) 7-(N,N,N-Triethylglycyloxymethyl)-1-methyl-3-isobutylxanthine chloride
(101) 7-($\alpha$-Ethoxyethyl)-1-methyl-3-isobutylxanthine
(102) 7-($\alpha$-Benzyloxyethyl)-1-methyl-3-isobutylxanthine
(103) 7-($\alpha$-Acetyloxyethyl)-1-methyl-3-isobutylxanthine
(104) 7-($\alpha$-Propionyloxyethyl)-1-methyl-3-isobutylxanthine
(105) 7-($\alpha$-Butanoyloxyethyl)-1-methyl-3-isobutylxanthine
(106) 7-($\alpha$-Pivalyloxyethyl)-1-methyl-3-isobutylxanthine
(107) 7-($\alpha$-Hexanoyloxyethyl)-1-methyl-3-isobutylxanthine
(108) 7-($\alpha$-Octanoyloxyethyl)-1-methyl-3-isobutylxanthine
(109) 7-($\alpha$-Ethoxycarbonyloxyethyl)-1-methyl-3-isobutylxanthine
(110) 7-[$\alpha$-(N,N-Dimethylglycyloxy)ethyl]-1-methyl-3-isobutylxanthine
(111) 7-[$\alpha$-(1-Piperidylacetyloxy)ethyl]-1-methyl-3-isobutylxanthine
(112) 7-($\alpha$-Benzoyloxyethyl)-1-methyl-3-isobutylxanthine
(113) 7-($\alpha$-Picolinoyloxyethyl)-1-methyl-3-isobutylxanthine
(114) 7-[$\alpha$-(N-Formylglycyloxy)ethyl]-1-methyl-3-isobutylxanthine
(115) 7-[$\alpha$-(N-Benzyloxycarbonylglycyloxy)ethyl]-1-methyl-3-isobutylxanthine
(116) 7-($\alpha$-Methylsuccinyloxyethyl)-1-methyl-3-isobutylxanthine
(117) 7-[$\alpha$-(N,N-Dimethylsuccinmyloxy)ethyl]-1-methyl-3-isobutylxanthine
(118) 7-[$\alpha$-(N,N,N-Trimethylglycyloxy)ethyl]-1-methyl-3-isobutylxanthine chloride
(119) 7-($\alpha$-Ethoxybenzyl)-1-methyl-3-isobutylxanthine
(120) 7-($\alpha$-Benzyloxybenzyl)-1-methyl-3-isobutylxanthine
(121) 7-($\alpha$-Acetyloxybenzyl)-1-methyl-3-isobutylxanthine
(122) 7-($\alpha$-Propionyloxybenzyl)-1-methyl-3-isobutylxanthine
(123) 7-($\alpha$-Butanoyloxybenzyl)-1-methyl-3-isobutylxanthine
(124) 7-($\alpha$-Pivalyloxybenzyl)-1-methyl-3-isobutylxanthine
(125) 7-($\alpha$-Hexanoyloxybenzyl)-1-methyl-3-isobutylxanthine
(126) 7-($\alpha$-Octanoyloxybenzyl)-1-methyl-3-isobutylxanthine
(127) 7-($\alpha$-Ethoxycarbonyloxybenzyl)-1-methyl-3-isobutylxanthine
(128) 7-[$\alpha$-(N,N-Dimethylglycyloxy)benzyl]-1-methyl-3-isobutylxanthine
(129) 7-[$\alpha$-(1-Piperidylacetyloxy)benzyl]-1-methyl-3-isobutylxanthine
(130) 7-($\alpha$-Benzoyloxybenzyl)-1-methyl-3-isobutylxanthine
(131) 7-($\alpha$-Picolinoyloxybenzyl)-1-methyl-3-isobutylxanthine
(132) 7-[$\alpha$-(N-Formylglycyloxy)benzyl]-1-methyl-3-isobutylxanthine
(133) 7-[$\alpha$-(N-Benzylaxycarbonylglycyloxy)benzyl]-1-methyl-3-isobutylxanthine
(134) 7-($\alpha$-Methylsuccinyloxybenzyl)-1-methyl-3-isobutylxanthine
(135) 7-[$\alpha$-(N,N-Dimethylsuccinamyloxy)benzyl]-1-methyl-3-isobutylxanthine
(136) 7-[$\alpha$-(N,N,N-Trimethylglycyloxy)benzyl]-1-methyl-3-isobutylxanthine chloride
(137) 7-Acetylthiomethyl-theophylline
(138) 7-Propionylthiomethyl-theophylline
(139) 7-Butanoylthiomethyl-theophylline
(140) 7-Pivalylthiomethyl-theophylline
(141) 7-Hexanoylthiomethyl-theophylline
(142) 7-Heptanoylthiomethyl-theophylline
(143) 7-Octanoylthiomethyl-theophylline
(144) 7-(N,N-Dimethylglycylthiomethyl)-theophylline
(145) 7-(1-Piperidylacetylthiomethyl)-theophylline
(146) 7-Benzoylthiomethyl-theophylline
(147) 7-p-Toluylthiomethyl-theophylline
(148) 7-Phenylacetylthiomethyl-theophylline
(149) 7-Picolinoylthiomethyl-theophylline
(150) 7-Nicotinoylthiomethyl-theophylline
(151) 7-N-Formylglycylthiomethyl-theophylline
(152) 7-Glycylthiomethyl-theophylline
(153) 7-Cinnamoylthiomethyl-theophylline
(154) 7-(N,N-Diethylsuccinamylthiomethyl)-theophylline
(155) 7-(N,N,N-Trimethylglycylthiomethyl)-theophylline chloride
(156) 7-(N,N,N-Triethylglycylthiomethyl)-theophylline chloride
(157) 7-(N,N-Diethylaminomethyl)-theophylline
(158) 7-(N-Methylacetamidomethyl)-theophylline
(159) 7-(N,N,-Diethylglycylamidomethyl)-theophylline
(160) 7-(N,N-Diethylamidosuccinamylamidomethyl)-theophylline From among the foregoing compounds, certain selected compounds are preferred and are claimed herein.

The compounds of the instant invention are easily prepared in accordance with those step-wise procedures outlined below.

The majority of those compounds encompassed within the above-described generic formula are prepared using two basic approaches. For convenience, theophylline will be employed as a model xanthine compound in the reaction schemes which follow:

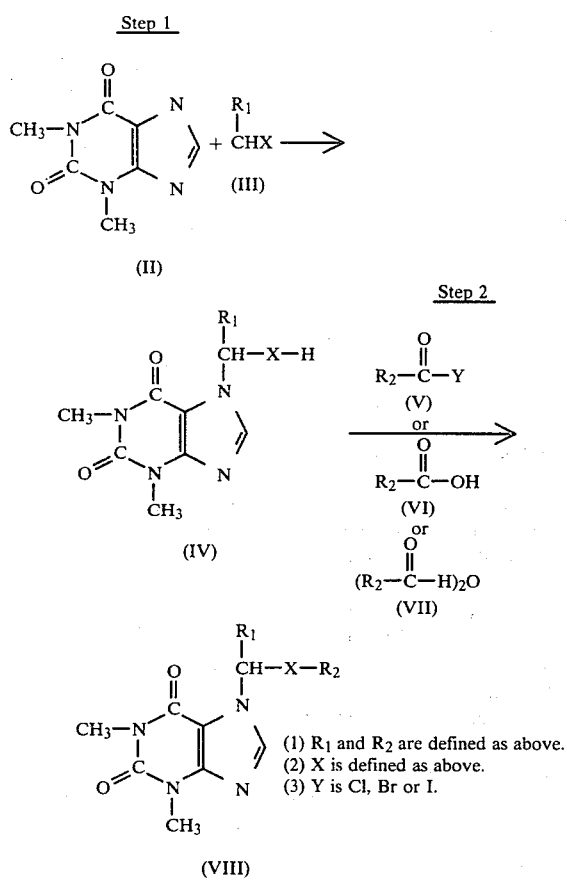

Step (1) is carried out in aqueous solution, using an excess of the aldehyde. The reaction is carried out at a temperature of from 0° C. to 100° C., at standard pressure, over a period of time ranging from one to 24 hours and further, in the presence of a basic catalyst such as trimethylamine, triethylamine, N-methylmorpholine, etc.

Alternatively, the same reaction can be carried out in the presence of a suitable organic solvent such as benzene, dimethylformamide, chloroform, etc., between room temperature and the boiling point of the solvent employed, standard pressure, and over a period of time ranging from one to 24 hours, employing a basic catalyst as described above, or an acid catalyst such as p-toluenesulfonic acid, $ZnCl_2$, sulfosalicylic acid, etc. In this procedure, an excess of aldehyde is required. As a second alternative, the same reaction can be carried out in the absence of a solvent or an excess of aldehyde when the aldehyde is employed as a solvent, per se. The reaction conditions employed are synonymous with those employed in the first alternative procedure described above. In addition, in this alternative procedure, the need for a basic or acid catalyst is optional.

The compound of formula IV obtained from step (1) can be isolated via standard crystallization procedures, and if need be, the compound can be recrystallized from any suitable anhydrous organic solvent such as benzene, tetrahydrofuran, acetone, chloroform, etc.

In step (2), acylation is carried out conventionally. For instance, one may react the product obtained from step (1) with a compound designated as

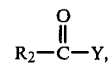

wherein Y is defined as above, in the presence of any suitable organic halocarbon solvent such as chloroform, dichloromethane, etc. and an acid scavenger such as trimethylamine, triethylamine, N-methylmorpholine, etc. The reaction is carried out at standard pressure, over a temperature range of from 0° C. to the boiling point of the solvent employed and for a period of time ranging from one to 24 hours.

In an alternative procedure, the product of step (1) can be reacted with a compound designated as

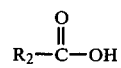

in the presence of an organic halocarbon solvent as described above, e.g., tetrahydrofuran, dioxane, etc. and a dehydrating agent such as dicyclohexylcarbodiimide (DCCI), 2-ethoxycarbonylethoxydihydroquinidine (EEDQ). This reaction is carried out at room temperature, standard pressure, and over a period of time ranging from one to 24 hours.

Finally, and yet another alternative procedure, the product of step (1) can be reacted with a compound designated as

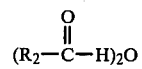

in the presence of any organic solvent noted above and in the further presence of an organic base such as trimethylamine, triethylamine, pyridine, etc. The reaction conditions employed are those of standard pressure and room temperature with a reaction time of one to 24 hours.

The compound of formula (VIII) can be obtained via standard crystallization procedures, and if necessary, recrystallization can be carried out in the presence of a suitable anhydrous organic solvent as illustrated earlier.

The second procedure for preparing the majority of those compounds encompassed by the above-described generic formula is illustrated below:

REACTION "A"

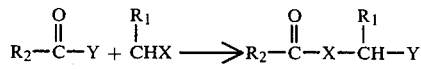

REACTION "B"

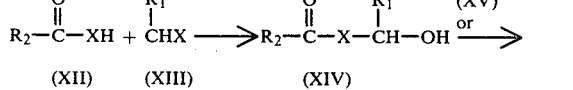

REACTION "C"

-continued

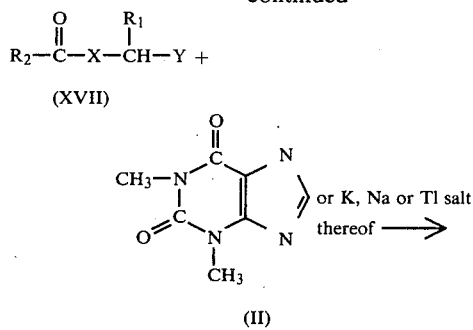

(1) R₁ and R₂ are as defined above.
(2) X and Y are as defined above.

In reaction "A", equimolar amounts of the compound of formula (IX) and (X) are reacted in the neat state in the presence of a Lewis acid catalyst such as ZnCl₂ or alternatively, in the presence of an organic solvent such as diethylether, dioxane, tetrahydrofuran, etc. The reaction is carried out at standard pressure, approximately 100° C., and over a period of time ranging from one to 24 hours. The product obtained from this reaction, i.e., the compound of formula (XI) is isolated via crystallization or fractional distillation from a suitable organic solvent such as hexane, heptane, benzene, etc.

In reaction "B", equimolar amounts of the compound of formula (XII) and (XIII) are reacted in the neat state under the same conditions and environment noted above in reaction "A" with the exception that the need for a Lewis acid catalyst does not exist. The compound obtained [the compound of formula (XIV)] is isolated via fractional distillation or crystallization. This compound is then reacted with PCl₅, PBr₅ or PI₅ at standard pressure, room temperature, and over a period of time ranging from one to 24 hours to obtain the compound of formula (XVI).

In reaction "C", the compounds of formula (XI) and (XVI) are then reacted with theophylline or the K, Na or Tl salt thereof in the presence of a suitable organic solvent such as acetone, dimethylformamide, tetrahydrofuran, etc., at standard pressure, over a temperature range of from 0° C. to the boiling point of the solvent, over a period of from one to 24 hours, and further, in the presence of trimethylamine, triethylamine, or any other equivalent organic base.

As for the remaining compounds of the above-described generic formula, they can be prepared in accordance with the reaction scheme outlined below:

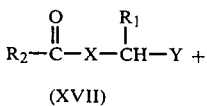

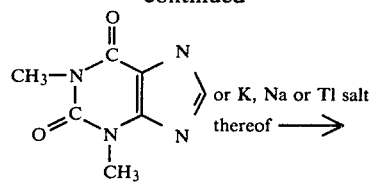

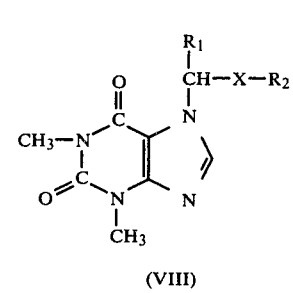

(1) R₁ and R₂ are as defined above.
(2) X and Y are as defined above.

The above reaction is carried out under the same conditions and environment described for reaction "B" of the alternative reaction procedure for preparing the majority of the compounds encompassed within the above-described generic formula noted above.

Without further elaboration, it is believed that one of ordinary skill in the art can, using the preceding description, utilize the instant invention to its utmost extent. The following preferred specific embodiments are, therefore, to be construed as merely illustrative, and not limitative of the remainder of the specification and claims in any way whatsoever. All references to "temperature" in the following examples denote Centigrade.

EXAMPLE I

Preparation of 7-Ethoxymethyl theophylline

A suspension of 7.20 g (0.04 mole) of theophylline and 2.76 g (0.02 mole) of K₂CO₃ in 200 ml of acetone was refluxed for two days and subsequently refluxed with 4.40 g (0.046 mole) of ethoxymethyl chloride for two days more. The suspension was filtered and the filtrate was concentrated in vacuo.

The residue was chromatographed on silica gel usisng diethyletheracetone (50:1) to acetone as the eluents. The first fraction that was obtained was the desired 7-ethoxymethyl theophylline (3.43 g, mp 110°–112° C., 35% yield). The product was recrystallized from dichloromethaneheptane to give 2.80 g (mp 111°–113° C.) of 7-ethoxymethyl theophylline which had the correct elemental analysis.

Anal. Calcd for C₁₀H₁₄N₄O₃: C, 50.41; N, 5.92; N, 23.52. Found: C, 50.59; H, 5.99; N, 23.58.

EXAMPLE II

Preparation of 7-Pivaloxymethyl theophylline

A suspension of 3.60 g (0.02 mole) of theophylline and 1.38 g (0.01 mole) of K₂CO₃ in 75 ml of acetone was refluxed overnight and then allowed to react at reflux with 3.00 g (0.02 mole) of pivaloxymethyl chloride for 2 days. The suspension was filtered and the residue was washed with acetone (200 ml). The combined filtrate and wash was concentrated in vacuo and the residue was extracted with boiling heptane (200 ml). The heptane solution was cooled in the refrigerator for 0.5 hr then filtered. The residue was dried in vacuo to give 1.50 g (mp 108°–109.5°) of 7-pivaloxymethyl theophylline.

Anal. Calcd for $C_{13}H_{18}N_4O_4$: C, 53.05; H, 6.16; N, 1904. Found: C, 53.06; H, 6.20; N, 19.32.

EXAMPLE III

Preparation of 7(1pyridyl)methyl theophylline chloride

A suspension of 3.60 g (0.02 mole) of theophylline, 2.30 g (0.02 mole) of pyridine hydrochloride and 0.7 g (0.023 mole) of paraformaldehyde was heated at 80° for 24 hr. Upon cooling, crystals immediately formed in the solution. The crystals were filtered and dried in vacuo to give 4.83 g (28% yield) of the desired compound as its hydrate.

Anal. Calcd for $C_{13}H_{14}N_5O_2Cl.H_2O$: C, 47.93; H, 4.95; N, 21.50. Found: C, 47.89; H, 4.98, N, 21.61.

EXAMPLE IV

Preparation of 7-Hexanoyloxymethyl theophylline

To 0.71 g (0.0053 mole) of hexanoyl chloride in 10 ml of $CH_2Cl_2$ there was added 1.10 g (0.0052 mole) of 7-hydroxymethyl theophylline; no reaction occurred and the reaction mixture was a suspension. Then 0.58 g (0.0057 mole) of triethylamine was added and a clear, colorless solution was obtained. The solution was stirred at room temperature for 15 minutes then concentrated in vacuo. The residue was titrated with 200 ml ether and filtered. The filtrate was concentrated in vacuo to give an oil which was titrated with heptane $CH_2Cl_2$(50:10). The resulting suspension was filtered while hot and concentrated to 20 ml, then cooled to room temperature. A gelatinous mass precipitated which was filtered and dried to give 0.70 g (mp 67°–72° C., 43% yield) of the desired product.

Anal. Calcd for $C_{14}H_{20}N_4O_4$: C, 54.53, H, 6.54; N, 18.17. Found: C, 54.58; H, 6.53; N, 18.35.

By following the preceding examples and substituting the appropriate generically or specifically described reactants and/or operating conditions of the instant invention, the following additional compounds were prepared:

(1) 7-Octanoyloxymethyl theophylline: 46% yield, mp 79°–82°.

Anal. Calcd for $C_{16}H_{24}N_4O_4$: C, 57.13; H, 7.19; N, 16.66. Found: C, 56.91; H, 7.23; N, 17.03.

(2) 7-Butanoyloxymethyl theophylline: 44% yield, mp 104°–105°.

Anal. Calcd for $C_{12}H_{16}N_4O_4$: C, 51.42; H, 5.68; N, 19.99. Found. C, 51.11; H, 5.80; N, 20.35.

(3) 7-Ethoxycarbonoyloxymethyl theophylline: 33% yield, mp 126.5°–127.5°.

Anal. Calcd for $C_{11}H_{14}N_4O_5$: C, 46.81; H, 5.00; N, 19.85. Found: C, 46.53; H, 4.99; N, 20.07.

EXAMPLE V

Preparation of 7-(N,N-Diethylsuccinamyloxymethyl)theophylline

To a mixture of 0.86 g (0.005 mole) of the diethylamide of succinic acid was added 1.05 g (0.005 mole) of 7-hydroxymethyl theophylline and 1.1 g (0.0055 mole) of dicyclohexylcarbodiimide in 10 ml of $CH_2Cl_2$ and 1.5 ml of pyridine. The suspension was stirred at room temperature overnight then filtered. The filtrate was concentrated in vacuo to give an oil. The oil was crystallized from diethylether to give the product as white crystals, mp 100°–103° C.

Anal. Calcd for $C_{16}H_{23}N_5O_5$: C, 52.59; H, 6.34; N, 19.44. Found: C, 52.28; H, 6.22; N, 19.35.

EXAMPLE VI

Preparation of 7-(N,N-Dimethylglycyloxymethyl)theophylline

To a mixture of 2.05 g (0.0097 mole) of 7-hydroxymethyl theophylline, 1.05 g (0.01 mole) of N,N-dimethylglycine and 2.25 g (0.011 mole) of dicyclohexylcarbodiimide was added 20 ml of pyridine; the resulting suspension was stirred at room temperature for 24 hr. The suspension was filtered and the filtrate was concentrated in vacuo to a solid residue. The residue was dissolved in $CH_2Cl_2$ (30 ml) and filtered. The $CH_2Cl_2$ solution was diluted with heptane (500 ml) until cloudy and allowed to sit at room temperature to crystallize. The crystals were filtered to give 2.00 g (mp 111°–113° C., 67% yield) of a light tan solid which was one spot upon analysis by thin layer chromatography (silica gel, acetone) and which had a nuclear magnetic resonance spectrum [($CDCl_3$)$\delta$7.88 (s,1, N—CH=N), 6.28 (s,2, N—$CH_2$—O), 3.60 (s,3, N—$CH_3$), 3.46 (s,3, N—$CH_3$), 3.25 (s,2, $CH_2$—N) and 2.37 (s,6, N—$CH_3$)] that was consistent with the structure of the desired product.

In similar fashion, the remaining compounds of the present invention can be prepared with similar success by merely following the preceding examples and substituting the generically and/or specifically described reactants and/or operating conditions of this invention for those of the preceding examples. Thus, the following additional compounds can be prepared by following the above reaction scheme:

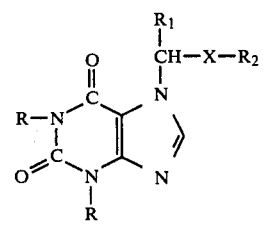

| R | | | | |
|---|---|---|---|---|
| N' | N³ | X | R₁ | R₂ |
| $CH_3$ | $CH_3$ | O | H | n-$C_3H_7$ |
| $CH_3$ | $CH_3$ | O | H | n-$C_4H_9$ |
| $CH_3$ | $CH_3$ | O | H | i-$C_4H_9$ |
| $CH_3$ | $CH_3$ | O | H | —$CH_2$—$C_6H_5$ |

-continued

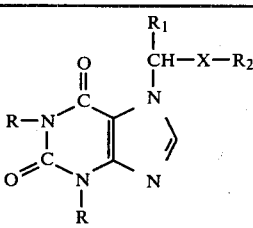

| N' | N³ | X | R₁ | R₂ |
|---|---|---|---|---|
| CH₃ | CH₃ | O | H | —CH₂—N(CH₃)₂ |
| CH₃ | CH₃ | O | H | —CH₂—N(C₂H₅)₂ |
| CH₃ | CH₃ | O | H | —CO—O—CH₂—C₆H₅ |
| CH₃ | CH₃ | O | H | —CO—O—CH₂—C(Cl)₃ |
| CH₃ | CH₃ | O | H | —CO—CH₂—N(C₂H₅)₂ |
| CH₃ | CH₃ | O | H | —CO—CH₂—N(piperidino) |
| CH₃ | CH₃ | O | H | —CO—C₆H₅ |
| CH₃ | CH₃ | O | H | —CO—C₆H₄—CH₃ |
| CH₃ | CH₃ | O | H | —CO—C₆H₄—OCH₃ |
| CH₃ | CH₃ | O | H | —CO—C₆H₄—N(CH₃)₂ |
| CH₃ | CH₃ | O | H | —CO—CH₂—C₆H₅ |
| CH₃ | CH₃ | O | H | —CO—(2-pyridyl) |
| CH₃ | CH₃ | O | H | —CO—(3-pyridyl) |
| CH₃ | CH₃ | O | H | —CO—CH₂—NH—HCO |
| CH₃ | CH₃ | O | H | —CO—CH₂—NH—CO—O—CH₂—C₆H₅ |
| CH₃ | CH₃ | O | H | —CO—CH₂—NH—CO—O—C₂H₅ |
| CH₃ | CH₃ | O | H | —CO—CH=CH—C₆H₅ |
| CH₃ | CH₃ | O | H | —CO—CH₂—COOCH₃ |
| CH₃ | CH₃ | O | H | —CO—CH₂—CH₂—CON(CH₃)₂ |
| CH₃ | CH₃ | O | H | —CO—CH₂—N⁺(CH₃)₃ · Y (Y = Cl, Br, I, etc.) |
| CH₃ | CH₃ | O | H | —CO—CH₂—N⁺(C₂H₅)₃ · Y (Y = Cl, Br, I, etc.) |
| CH₃ | CH₃ | O | H | —C₂H₄—N(CH₃)₂ |
| CH₃ | CH₃ | O | H | —CO—(N-oxide-pyrrolidinyl) |
| CH₃ | CH₃ | O | H | —SO₂—C₆H₄—CH₃ |
| CH₃ | CH₃ | O | CH₃ | n-C₃H₇ |
| CH₃ | CH₃ | O | CH₃ | n-C₄H₉ |

-continued

[Structure: xanthine/purine core with R on N1 and N3, and -CH(R1)-X-R2 substituent on N7]

| N' | N³ | X | R₁ | R₂ |
|---|---|---|---|---|
| CH₃ | CH₃ | O | CH₃ | i-C₄H₉ |
| CH₃ | CH₃ | O | CH₃ | —CH₂—C₆H₅ |
| CH₃ | CH₃ | O | CH₃ | —CH₂—N(CH₃)₂ |
| CH₃ | CH₃ | O | CH₃ | —CH₂—N(C₂H₅)₂ |
| CH₃ | CH₃ | O | CH₃ | —CO—O—CH₂—C₆H₅ |
| CH₃ | CH₃ | O | CH₃ | —CO—O—CH₂—CCl₃ |
| CH₃ | CH₃ | O | CH₃ | —CO—CH₂—N(C₂H₅)₂ |
| CH₃ | CH₃ | O | CH₃ | —CO—CH₂—N(piperidinyl) |
| CH₃ | CH₃ | O | CH₃ | —CO—C₆H₅ |
| CH₃ | CH₃ | O | CH₃ | —CO—C₆H₄—CH₃ |
| CH₃ | CH₃ | O | CH₃ | —CO—C₆H₄—OCH₃ |
| CH₃ | CH₃ | O | CH₃ | —CO—C₆H₄—N(CH₃)₂ |
| CH₃ | CH₃ | O | CH₃ | —CO—CH₂—C₆H₅ |
| CH₃ | CH₃ | O | CH₃ | —CO—(2-furyl/pyridyl ring with O, N) |
| CH₃ | CH₃ | O | CH₃ | —CO—(furyl/pyrrolyl ring with O, N) |
| CH₃ | CH₃ | O | CH₃ | —CO—CH₂—NH—HCO |
| CH₃ | CH₃ | O | CH₃ | —CO—CH₂—NH—CO—O—CH₂—C₆H₅ |
| CH₃ | CH₃ | O | CH₃ | —CO—CH₂—NH—CO—O—C₂H₅ |
| CH₃ | CH₃ | O | CH₃ | —CO—CH=CH—C₆H₅ |
| CH₃ | CH₃ | O | CH₃ | —CO—CH₂—CH₂—COOCH₃ |
| CH₃ | CH₃ | O | CH₃ | —CO—CH₂—CH₂—CON(CH₃)₂ |
| CH₃ | CH₃ | O | CH₃ | —CO—CH₂—$\overset{\oplus}{N}$(CH₃)₃ · Y (Y = Cl, Br, I, etc.) |
| CH₃ | CH₃ | O | CH₃ | —CO—CH₂—$\overset{\oplus}{N}$(C₂H₅)₃ · Y (Y = Cl, Br, I, etc.) |
| CH₃ | CH₃ | O | CH₃ | —C₂H₄—N(CH₃)₂ |
| CH₃ | CH₃ | O | CH₃ | —CO—(furyl/pyridinium ring with O, N⁺) |
| CH₃ | CH₃ | O | CH₃ | —SO₂—C₆H₄—CH₃ |

-continued

[Structure: xanthine with N1-R, N3-R, N7-CHR1-X-R2]

| R | | | | |
|---|---|---|---|---|
| N' | N³ | X | R₁ | R₂ |
| CH₃ | -CH₂-CH(CH₃)₂ | O | H | n-C₃H₇ |
| CH₃ | -CH₂-CH(CH₃)₂ | O | H | n-C₄H₉ |
| CH₃ | -CH₂-CH(CH₃)₂ | O | H | i-C₄H₉ |
| CH₃ | -CH₂-CH(CH₃)₂ | O | H | —CH₂—C₆H₅ |
| CH₃ | -CH₂-CH(CH₃)₂ | O | H | —CH₂—N(CH₃)₂ |
| CH₃ | -CH₂-CH(CH₃)₂ | O | H | —CH₂—N(C₂H₅)₂ |
| CH₃ | -CH₂-CH(CH₃)₂ | O | H | —CO—O—CH₂—C₆H₅ |
| CH₃ | -CH₂-CH(CH₃)₂ | O | H | —CO—O—CH₂—CCl₃ |
| CH₃ | -CH₂-CH(CH₃)₂ | O | H | —CO—CH₂—N(C₂H₅)₂ |
| CH₃ | -CH₂-CH(CH₃)₂ | O | H | —CO—CH₂—N(piperidine) |

-continued

[Structure: xanthine core with R on N1 and N3, and N-CH(R₁)-X-R₂ substituent]

| R N' | R N³ | X | R₁ | R₂ |
|---|---|---|---|---|
| CH₃ | -CH₂-CH(CH₃)₂ | O | H | -CO-C₆H₅ |
| CH₃ | -CH₂-CH(CH₃)₂ | O | H | -CO-C₆H₄-CH₃ |
| CH₃ | -CH₂-CH(CH₃)₂ | O | H | -CO-C₆H₄-OCH₃ |
| CH₃ | -CH₂-CH(CH₃)₂ | O | H | -CO-C₆H₄-N(CH₃)₂ |
| CH₃ | -CH₂-CH(CH₃)₂ | O | H | -CO-CH₂-C₆H₅ |
| CH₃ | -CH₂-CH(CH₃)₂ | O | H | -CO-(2-pyridyl) |
| CH₃ | -CH₂-CH(CH₃)₂ | O | H | -CO-(3-pyridyl) |
| CH₃ | -CH₂-CH(CH₃)₂ | O | H | -CO-CH₂-NH-HCO |
| CH₃ | -CH₂-CH(CH₃)₂ | O | H | -CO-CH₂-NH-CO-O-CH₂-C₆H₅ |
| CH₃ | -CH₂-CH(CH₃)₂ | O | H | -CO-CH₂-NH-CO-O-C₂H₅ |

-continued

[Structure: xanthine with R on N1 and N3, and CH(R1)-X-R2 on N7]

| N' | N³ | X | R₁ | R₂ |
|---|---|---|---|---|
| CH₃ | CH₂-CH(CH₃)₂ | O | H | —CO—CH=CH—C₆H₅ |
| CH₃ | CH₂-CH(CH₃)₂ | O | H | —CO—CH₂—CH₂—COOCH₃ |
| CH₃ | CH₂-CH(CH₃)₂ | O | H | —CO—CH₂—CH₂—CON(CH₃)₂ |
| CH₃ | CH₂-CH(CH₃)₂ | O | H | —CO—CH₂—N⁺(CH₃)₃ · Y (Y = Cl, Br, I, etc.) |
| CH₃ | CH₂-CH(CH₃)₂ | O | H | —CO—CH₂—N⁺(C₂H₅)₃ · Y (Y = Cl, Br, I, etc.) |
| CH₃ | CH₂-CH(CH₃)₂ | O | H | —C₂H₄—N(CH₃)₂ |
| CH₃ | CH₂-CH(CH₃)₂ | O | H | —CO—(pyridine N-oxide) |
| CH₃ | CH₂-CH(CH₃)₂ | O | H | —SO₂—C₆H₄—CH₃ |
| CH₃ | CH₂-CH(CH₃)₂ | O | CH₃ | n-C₃H₇ |
| CH₃ | CH₂-CH(CH₃)₂ | O | CH₃ | n-C₄H₉ |

-continued

[Structure: purine/xanthine derivative with substituents R, R, R1, X, R2 on the scaffold]

| N' | N³ | X | R₁ | R₂ |
|---|---|---|---|---|
| $CH_3$ | $-CH_2-CH(CH_3)_2$ | O | $CH_3$ | $i\text{-}C_4H_9$ |
| $CH_3$ | $-CH_2-CH(CH_3)_2$ | O | $CH_3$ | $-CH_2-C_6H_5$ |
| $CH_3$ | $-CH_2-CH(CH_3)_2$ | O | $CH_3$ | $-CH_2-N(CH_3)_2$ |
| $CH_3$ | $-CH_2-CH(CH_3)_2$ | O | $CH_3$ | $-CH_2-N(C_2H_5)_2$ |
| $CH_3$ | $-CH_2-CH(CH_3)_2$ | O | $CH_3$ | $-CO-O-CH_2-C_6H_5$ |
| $CH_3$ | $-CH_2-CH(CH_3)_2$ | O | $CH_3$ | $-CO-O-CH_2-CCl_3$ |
| $CH_3$ | $-CH_2-CH(CH_3)_2$ | O | $CH_3$ | $-CO-CH_2-N(C_2H_5)_2$ |
| $CH_3$ | $-CH_2-CH(CH_3)_2$ | O | $CH_3$ | $-CO-CH_2-N(\text{piperidinyl})$ |
| $CH_3$ | $-CH_2-CH(CH_3)_2$ | O | $CH_3$ | $-CO-C_6H_5$ |
| $CH_3$ | $-CH_2-CH(CH_3)_2$ | O | $CH_3$ | $-CO-C_6H_4-CH_3$ |

-continued

[Structure: xanthine core with N' bearing CH(R₁)-X-R₂ substituent, N³ bearing R, and another N bearing R]

| R | | | | |
|---|---|---|---|---|
| N' | N³ | X | R₁ | R₂ |
| CH₃ | CH₂-CH(CH₃)(CH₃) | O | CH₃ | —CO—C₆H₄—OCH₃ |
| CH₃ | CH₂-CH(CH₃)(CH₃) | O | CH₃ | —CO—C₆H₄—N(CH₃)₂ |
| CH₃ | CH₂-CH(CH₃)(CH₃) | O | CH₃ | —CO—CH₂—C₆H₅ |
| CH₃ | CH₂-CH(CH₃)(CH₃) | O | CH₃ | —CO—(2-pyridyl) |
| CH₃ | CH₂-CH(CH₃)(CH₃) | O | CH₃ | —CO—(3-pyridyl) |
| CH₃ | CH₂-CH(CH₃)(CH₃) | O | CH₃ | —CO—CH₂—NH—HCO |
| CH₃ | CH₂-CH(CH₃)(CH₃) | O | CH₃ | —CO—CH₂—NH—CO—O—CH₂—C₆H₅ |
| CH₃ | CH₂-CH(CH₃)(CH₃) | O | CH₃ | —CO—CH₂—NH—CO—O—C₂H₅ |
| CH₃ | CH₂-CH(CH₃)(CH₃) | O | CH₃ | —CO—CH=CH—C₆H₅ |
| CH₃ | CH₂-CH(CH₃)(CH₃) | O | CH₃ | —CO—CH₂—CH₂—COOCH₃ |

-continued

Structure: Xanthine derivative with N7-CH(R1)-X-R2, N1-R, N3-R substituents.

| N' | N³ | X | R₁ | R₂ |
|---|---|---|---|---|
| CH₃ | -CH₂-CH(CH₃)-CH₃ (isobutyl) | O | CH₃ | -CO-CH₂-CH₂-CON(CH₃)₂ |
| CH₃ | -CH₂-CH(CH₃)-CH₃ | O | CH₃ | -CO-CH₂-$\overset{\oplus}{N}$(CH₃)₃ · Y (Y = Cl, Br, I, etc.) |
| CH₃ | -CH₂-CH(CH₃)-CH₃ | O | CH₃ | -CO-CH₂-$\overset{\oplus}{N}$(C₂H₅)₃ · Y (Y = Cl, Br, I, etc.) |
| CH₃ | -CH₂-CH(CH₃)-CH₃ | O | CH₃ | -C₂H₄-N(CH₃)₂ |
| CH₃ | -CH₂-CH(CH₃)-CH₃ | O | CH₃ | -CO-(2,5-dihydroisoxazol-3-yl, N→O) |
| CH₃ | -CH₂-CH(CH₃)-CH₃ | O | CH₃ | -SO₂-C₆H₄-CH₃ |
| CH₃ | CH₃ | S | H | n-C₃H₇ |
| CH₃ | CH₃ | S | H | n-C₄H₉ |
| CH₃ | CH₃ | S | H | i-C₄H₉ |
| CH₃ | CH₃ | S | H | -CH₂-C₆H₅ |
| CH₃ | CH₃ | S | H | -CH₂-N(CH₃)₂ |
| CH₃ | CH₃ | S | H | -CH₂-N(C₂H₅)₂ |
| CH₃ | CH₃ | S | H | -CO-O-CH₂-C₆H₅ |
| CH₃ | CH₃ | S | H | -CO-O-CH₂-CCl₃ |
| CH₃ | CH₃ | S | H | -CO-CH₂-N(C₂H₅)₂ |
| CH₃ | CH₃ | S | H | -CO-CH₂-N(piperidinyl) |
| CH₃ | CH₃ | S | H | -CO-C₆H₅ |

-continued $$\begin{array}{c}\text{structure with } R_1\text{-CH-X-R}_2 \text{ substituent on xanthine core, } R \text{ on } N' \text{ and } N^3\end{array}$$

| R N' | R N³ | X | $R_1$ | $R_2$ |
|---|---|---|---|---|
| CH₃ | CH₃ | S | H | —CO—C₆H₄—CH₃ |
| CH₃ | CH₃ | S | H | —CO—C₆H₄—OCH₃ |
| CH₃ | CH₃ | S | H | —CO—C₆H₄—N(CH₃)₂ |
| CH₃ | CH₃ | S | H | —CO—CH₂—C₆H₅ |
| CH₃ | CH₃ | S | H | —CO—(2-pyridyl) |
| CH₃ | CH₃ | S | H | —CO—(3-pyridyl) |
| CH₃ | CH₃ | S | H | —CO—CH₂—NH—HCO |
| CH₃ | CH₃ | S | H | —CO—CH₂—NH—CO—O—CH₂—C₆H₅ |
| CH₃ | CH₃ | S | H | —CO—CH₂—NH—CO—O C₂H₅ |
| CH₃ | CH₃ | S | H | —CO—CH=CH—C₆H₅ |
| CH₃ | CH₃ | S | H | —CO—CH₂—CH₂—COOCH₃ |
| CH₃ | CH₃ | S | H | —CO—CH₂—CH₂—CON(CH₃)₂ |
| CH₃ | CH₃ | S | H | —CO—CH₂—N⊕(CH₃)₃ · Y (Y = Cl, Br, I, etc.) |
| CH₃ | CH₃ | S | H | —CO—CH₂—N⊕(C₂H₅)₃ · Y (Y = Cl, Br, I, etc.) |
| CH₃ | CH₃ | S | H | —C₂H₄—N(CH₃)₂ |
| CH₃ | CH₃ | S | H | —CO—(pyridyl N-oxide) |
| CH₃ | CH₃ | S | H | —SO₂—C₆H₄—CH₃ |
| CH₃ | CH₃ | S | CH₃ | n-C₃H₇ |
| CH₃ | CH₃ | S | CH₃ | n-C₄H₉ |
| CH₃ | CH₃ | S | CH₃ | i-C₄H₉ |
| CH₃ | CH₃ | S | CH₃ | —CH₂—C₆H₅ |
| CH₃ | CH₃ | S | CH₃ | —CH₂—N(CH₃)₂ |
| CH₃ | CH₃ | S | CH₃ | —CH₂—N(C₂H₅)₂ |
| CH₃ | CH₃ | S | CH₃ | —CO—O—CH₂—C₂H₅ |
| CH₃ | CH₃ | S | CH₃ | —CO—O—CH₂—C(Cl)₃ |
| CH₃ | CH₃ | S | CH₃ | —CO—CH₂—N(C₂H₅)₂ |

-continued $$\begin{array}{c} \text{structure with } R_1, X, R_2 \text{ substituents on xanthine core} \end{array}$$

| R N' | R N³ | X | R₁ | R₂ |
|---|---|---|---|---|
| CH₃ | CH₃ | S | CH₃ | —CO—CH₂—N(piperidine) |
| CH₃ | CH₃ | S | CH₃ | —CO—C₆H₅ |
| CH₃ | CH₃ | S | CH₃ | —CO—C₆H₄—CH₃ |
| CH₃ | CH₃ | S | CH₃ | —CO—C₆H₄—OCH₃ |
| CH₃ | CH₃ | S | CH₃ | —CO—C₆H₄—N(CH₃)₂ |
| CH₃ | CH₃ | S | CH₃ | —CO—CH₂—C₆H₅ |
| CH₃ | CH₃ | S | CH₃ | —CO—(pyridyl) |
| CH₃ | CH₃ | S | CH₃ | —CO—(pyridyl) |
| CH₃ | CH₃ | S | CH₃ | —CO—CH₂—NH—HCO |
| CH₃ | CH₃ | S | CH₃ | —CO—CH₂—NH—CO—O—CH₂—C₆H₅ |
| CH₃ | CH₃ | S | CH₃ | —CO—CH₂—NH—CO—O—C₂H₅ |
| CH₃ | CH₃ | S | CH₃ | —CO—CH=CH—C₆H₅ |
| CH₃ | CH₃ | S | CH₃ | —CO—CH₂—CH₂—COOCH₃ |
| CH₃ | CH₃ | S | CH₃ | —CO—CH₂—CH₂—CON(CH₃)₂ |
| CH₃ | CH₃ | S | CH₃ | —CO—CH₂—N⁺(CH₃)₃ · Y (Y = Cl, Br, I, etc.) |
| CH₃ | CH₃ | S | CH₃ | —CO—CH₂—N⁺(C₂H₅)₃ · Y (Y = Cl, Br, I, etc.) |
| CH₃ | CH₃ | S | CH₃ | —C₂H₄—N(CH₃)₂ |
| CH₃ | CH₃ | S | CH₃ | —CO—(pyridyl N-oxide) |
| CH₃ | CH₃ | S | CH₃ | —SO₂—C₆H₄—CH₃ |
| CH₃ | —CH₂—CH(CH₃)—CH(CH₃)₂ | S | H | n-C₃H₇ |
| CH₃ | —CH₂—CH(CH₃)—CH(CH₃)₂ | S | H | n-C₄H₉ |
| CH₃ | —CH₂—CH(CH₃)—CH(CH₃)₂ | S | H | i-C₄H₉ |

-continued $$\begin{array}{c}\text{structure: 7-substituted xanthine with } N^7\text{-CH}(R_1)\text{-X-}R_2,\ N^1\text{-R},\ N^3\text{-R}\end{array}$$

| N' | N³ | X | R₁ | R₂ |
|---|---|---|---|---|
| CH₃ | -CH₂-CH(CH₃)₂ | S | H | -CH₂-C₆H₅ |
| CH₃ | -CH₂-CH(CH₃)₂ | S | H | -CH₂-N(CH₃)₂ |
| CH₃ | -CH₂-CH(CH₃)₂ | S | H | -CH₂-N(C₂H₅)₂ |
| CH₃ | -CH₂-CH(CH₃)₂ | S | H | -CO-O-CH₂-C₆H₅ |
| CH₃ | -CH₂-CH(CH₃)₂ | S | H | -CO-O-CH₂-CCl₃ |
| CH₃ | -CH₂-CH(CH₃)₂ | S | H | -CO-CH₂-N(C₂H₅)₂ |
| CH₃ | -CH₂-CH(CH₃)₂ | S | H | -CO-CH₂-N(piperidinyl) |
| CH₃ | -CH₂-CH(CH₃)₂ | S | H | -CO-C₆H₅ |
| CH₃ | -CH₂-CH(CH₃)₂ | S | H | -CO-C₆H₄-CH₃ |
| CH₃ | -CH₂-CH(CH₃)₂ | S | H | -CO-C₆H₄-OCH₃ |

-continued $$\text{structure: xanthine/purine with R on N1, R on N3, and N7-CH(R}_1\text{)-X-R}_2\text{ substituent}$$

| N' (R) | N³ (R) | X | R₁ | R₂ |
|---|---|---|---|---|
| CH₃ | -CH₂-CH(CH₃)₂ | S | H | -CO-C₆H₄-N(CH₃)₂ |
| CH₃ | -CH₂-CH(CH₃)₂ | S | H | -CO-CH₂-C₆H₅ |
| CH₃ | -CH₂-CH(CH₃)₂ | S | H | -CO-(2-pyridyl) |
| CH₃ | -CH₂-CH(CH₃)₂ | S | H | -CO-(3-pyridyl) |
| CH₃ | -CH₂-CH(CH₃)₂ | S | H | -CO-CH₂-NH-HCO |
| CH₃ | -CH₂-CH(CH₃)₂ | S | H | -CO-CH₂-NH-CO-O-CH₂-C₆H₅ |
| CH₃ | -CH₂-CH(CH₃)₂ | S | H | -CO-CH₂-NH-CO-O-C₂H₅ |
| CH₃ | -CH₂-CH(CH₃)₂ | S | H | -CO-CH=CH-C₆H₅ |
| CH₃ | -CH₂-CH(CH₃)₂ | S | H | -CO-CH₂-CH₂-COOCH₃ |
| CH₃ | -CH₂-CH(CH₃)₂ | S | H | -CO-CH₂-CH₂-CON(CH₃)₂ |

-continued

Structure: 7-substituted xanthine with R at N1 and N3, and CH(R1)-X-R2 at N7.

| N' | N³ | X | R₁ | R₂ |
|---|---|---|---|---|
| CH₃ | -CH₂-CH(CH₃)₂ | S | H | $-CO-CH_2-\overset{\oplus}{N}(CH_3)_3 \cdot Y$ (Y = Cl, Br, I, etc.) |
| CH₃ | -CH₂-CH(CH₃)₂ | S | H | $-CO-CH_2-\overset{\oplus}{N}(C_2H_5)_3 \cdot Y$ (Y = Cl, Br, I, etc.) |
| CH₃ | -CH₂-CH(CH₃)₂ | S | H | $-C_2H_4-N(CH_3)_2$ |
| CH₃ | -CH₂-CH(CH₃)₂ | S | H | -CO-(2,5-dihydroisoxazole N-oxide) |
| CH₃ | -CH₂-CH(CH₃)₂ | S | H | $-SO_2-C_6H_4-CH_3$ |
| CH₃ | -CH₂-CH(CH₃)₂ | S | CH₃ | n-C₃H₇ |
| CH₃ | -CH₂-CH(CH₃)₂ | S | CH₃ | n-C₄H₉ |
| CH₃ | -CH₂-CH(CH₃)₂ | S | CH₃ | i-C₄H₉ |
| CH₃ | -CH₂-CH(CH₃)₂ | S | CH₃ | $-CH_2-C_6H_5$ |
| CH₃ | -CH₂-CH(CH₃)₂ | S | CH₃ | $-CH_2-N(CH_3)_2$ |

-continued

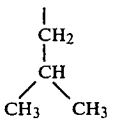

| N' | R N³ | X | R₁ | R₂ |
|---|---|---|---|---|
| CH₃ | CH₂—CH(CH₃)(CH₃) | S | CH₃ | —CH₂—N(C₂H₅)(C₂H₅) |
| CH₃ | CH₂—CH(CH₃)(CH₃) | S | CH₃ | —CO—O—CH₂—C₆H₅ |
| CH₃ | CH₂—CH(CH₃)(CH₃) | S | CH₃ | —CO—O—CH₂—C(Cl)(Cl)(Cl) |
| CH₃ | CH₂—CH(CH₃)(CH₃) | S | CH₃ | —CO—CH₂—N(C₂H₅)(C₂H₅) |
| CH₃ | CH₂—CH(CH₃)(CH₃) | S | CH₃ | —CO—CH₂—N(piperidine) |
| CH₃ | CH₂—CH(CH₃)(CH₃) | S | CH₃ | —CO—C₆H₅ |
| CH₃ | CH₂—CH(CH₃)(CH₃) | S | CH₃ | —CO—C₆H₄—CH₃ |
| CH₃ | CH₂—CH(CH₃)(CH₃) | S | CH₃ | —CO—C₆H₄—OCH₃ |
| CH₃ | CH₂—CH(CH₃)(CH₃) | S | CH₃ | —CO—C₆H₄—N(CH₃)(CH₃) |
| CH₃ | CH₂—CH(CH₃)(CH₃) | S | CH₃ | —CO—CH₂—C₆H₅ |

-continued $$\underset{\underset{R}{N}}{\overset{O}{\underset{\|}{C}}}\text{-xanthine core with } R_1, X, R_2 \text{ substituents}$$

| N' | N³ (R) | X | R₁ | R₂ |
|---|---|---|---|---|
| CH₃ | CH₂-CH(CH₃)₂ | S | CH₃ | -CO-(2-furyl/pyridyl ring with O, N) |
| CH₃ | CH₂-CH(CH₃)₂ | S | CH₃ | -CO-(3-pyridyl/furyl ring with O, N) |
| CH₃ | CH₂-CH(CH₃)₂ | S | CH₃ | -CO-CH₂-NH-HCO |
| CH₃ | CH₂-CH(CH₃)₂ | S | CH₃ | -CO-CH₂-NH-CO-O-CH₂-C₆H₅ |
| CH₃ | CH₂-CH(CH₃)₂ | S | CH₃ | -CO-CH₂-NH-CO-O-C₂H₅ |
| CH₃ | CH₂-CH(CH₃)₂ | S | CH₃ | -CO-CH=CH-C₆H₅ |
| CH₃ | CH₂-CH(CH₃)₂ | S | CH₃ | -CO-CH₂-CH₂-COOCH₃ |
| CH₃ | CH₂-CH(CH₃)₂ | S | CH₃ | -CO-CH₂-CH₂-CON(CH₃)₂ |
| CH₃ | CH₂-CH(CH₃)₂ | S | CH₃ | -CO-CH₂-N⁺(CH₃)₃ · Y (Y = Cl, Br, I, etc.) |
| CH₃ | CH₂-CH(CH₃)₂ | S | CH₃ | -CO-CH₂-N⁺(C₂H₅)₃ · Y (Y = Cl, Br, I, etc.) |

-continued

[Structure: theophylline-like core with R-N, N-R substituents, and CH(R₁)-X-R₂ group on the imidazole nitrogen]

| N' | N³ | X | R₁ | R₂ |
|---|---|---|---|---|
| CH₃ | CH₂-CH(CH₃)-CH₃ (isobutyl with extra CH₂) | S | CH₃ | —C₂H₄—N(CH₃)₂ |
| CH₃ | CH₂-CH(CH₃)-CH₃ | S | CH₃ | —CO—(N-oxide pyrrolidinyl) |
| CH₃ | CH₂-CH(CH₃)-CH₃ | S | CH₃ | —SO₂—C₆H₄—CH₃ |

EXAMPLE VII

Partition Coefficient Studies

That the compounds of the instant invention are suitable for dermal application and penetration is established by determining their partition coefficient values in water/heptane versus water and heptane, per se, as illustrated in Table I below. Certain derivatives of Formula (I) must have a coefficient value of from 0.05 to 6.5. Other derivatives of Formula (I) will exhibit varying coefficient values, but do, in fact, penetrate the dermal membrane. Their mechanism of penetration has not been determined.

TABLE I $$thCH_2OC(=O)-R$$

| | Water mg/ml | Heptane mg/ml | Water/ Heptane |
|---|---|---|---|
| R = C₃H₇ | 3.89 | 0.65 | 6.30 |
| = C(CH₃)₃ | 2.01 | 1.55 | 1.11 |
| = C₅H₁₁ | 0.11 | 2.26 | 0.42 |
| = C₇H₁₅ | 0.12 | 0.52 | 0.06 |
| = —OC₂H₅ | 3.87 | 0.18 | 32.0 |
| = CH₂N(CH₃)₂ | >1 g/ml | <10 mg/ 500 ml | |
| = CH₂CH₂C(=O)N(C₂H₅)₂ | 26.3 | 0.17 | 25.0 | th = 7-theophylline

EXAMPLE VIII

Dermal Anti-inflammatory Studies

Using the standard "earburn" test for establishing anti-inflammatory activity, each of the compounds of Table I of Example VII were tested against theophylline per se for anti-inflammatory activity. Specifically, the right ear of a rat is placed between two metal cylinders held together by a force of 2 lbs. The cylinder is heated to 51.6° C. by circulating water from a constant temperature bath. The ear is burned for 10 seconds and then treated one minute later with 50 μl of drug at a concentration of 0.003 M, dissolved in isopropylmyristate. Five hours after the burn, the animals are sacrificed and the ears are removed using anatomical guidelines. The % increase in weight of the right ear over the left ear is determined. The anti-inflammatory activity of the tested compounds is determined by their ability to reduce the increase in ear weight produced by the burn as a result of subsequent edema.

With the exception of theophylline, all compounds tested effected a substantial reduction in ear weight. When the above study is repeated, but this time substituting the remaining compounds of Formula (I) for those of Table I, substantially similar results are obtained.

At this point, it should again be emphasized that for certain compounds of Formula (I), a Heptane/Water coefficient of 0.05-6.5 is exhibited and mandatory for dermal penetration. Insofar as other compounds of Formula (I) are concerned, while their heptane/water coefficient is not critical and will vary widely, dermal penetration is nevertheless achieved.

Similarly, while dermal anti-inflammatory activity is demonstrated for all the compounds of Formula (I), no definite mechanism of action has yet been established.

Repeating the above partition studies with the remaining compounds of the present invention will yield partition coefficient values similar to those noted above.

The compounds of the present invention are conveniently administered to warm-blooded animals via topical administration with any suitable pharmaceutically acceptable topical carrier material. Such carrier materials are well known to those skilled in the art of topical pharmaceutical formulations. For those not skilled in the art, reference is made to the text entitled, "Remington's Pharmaceutical Sciences" (Fourteenth Edition), 1970 and U.S. Pat. No. 3,849,553. In a typical preparation for topical application, any one of the compounds of the instant invention is combined with triacetin such that the active ingredient approximates a concentration of from 1 to 5 percent. The preparation is simply applied topically to the inflamed or psoriatic area whereby the therapeutically active compound is dermally absorbed and cleaved to release the parent xanthine moiety. Naturally, the topical administrative regimen of the compounds of the instant application will vary with the degree of the inflammatory condition being treated. As such, frequency of administration is left to the physician or individual being treated. The dosage administered is not subject to definite bounds, but it will usually be an effective amount, or the equivalent on a molar basis of the pharmacologically active form produced upon the metabolic release of the active drug to achieve its desired pharmacological and physiological effect.

If necessary, ancillary adjuvants may be added to the above-described topical formulation such as coloring agents, scenting agents and the like with the proviso that such adjuvants do not detract from the main purpose of the present invention, i.e., do not impede dermal absorption of the presently described compounds.

From the foregoing description, one of ordinary skill in the art can easily ascertain the essential characteristics of the instant invention, and without departing from the spirit and scope thereof, can make various changes and/or modifications of the invention to adapt it to various usages and conditions. As such, these changes and/or modifications are properly, equitably, and intended to be, within the full range of equivalence of the following claims.

What we claim is:

1. A pro-drug compound of the formula:

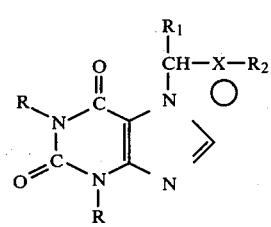
(I)

wherein R, which may be the same or different, represents a member selected from the group consisting of —CH$_3$, —C$_2$H$_5$, —C$_3$H$_7$, iso-C$_3$H$_7$, —C$_4$H$_9$, iso-C$_4$H$_9$, pentyl, benzyl, allyl, 2-hydroxyethyl, cyclohexyl, 2-isobutenyl, hydroxymethyl, 2-phenylethyl and —CH$_2$O—R$_2$, wherein R$_2$ is defined infra; wherein R$_1$ represents a member selected from the group consisting of H, C$_1$–C$_7$ straight or branched alkyl, CCl$_3$, CBr$_3$, CI$_3$,

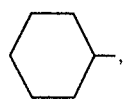

CH$_3$O—CH$_2$—, (CH$_3$)$_2$NCH$_2$—,

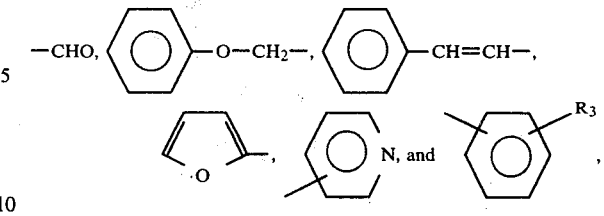

wherein R$_3$ represents a member selected from the group consisting of —OH, halogen,

—OCH$_3$,

—COOCH$_3$, —NO$_2$ and —OCOCH$_3$; wherein X is —O—, —S—, or

and wherein R$_2$ represents a member selected from the group consisting of

wherein R$_4$ is a member selected from the group consisting of C$_2$–C$_{20}$ straight or branched alkyl, cyclo(C$_3$–C$_{10}$)alkyl,

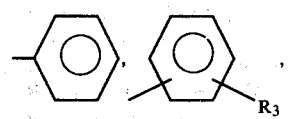

wherein R$_3$ is defined as above,

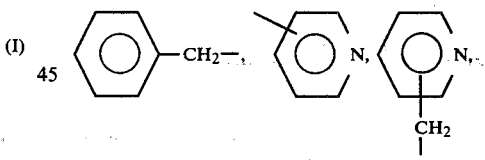

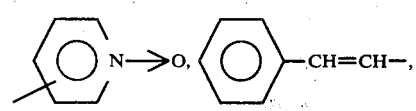

the residue of any naturally occurring amino acid, the residue of any N- substituted amino acid, wherein said substituent is any amino acid protective group cleavable via hydrogenolysis or hydrolysis, the residue of an N,N-C$_1$–C$_5$-dialkyl, cycloalkyl, N-heteroaromatic or N-C$_1$–C$_5$ alkyl aniline amino acid,

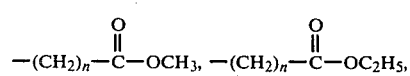

wherein n represents an integer of from 1–5 and $R_5$ and $R_6$ which may be the same or different represent $C_1$–$C_5$ alkyl or together form a heterocyclic ring with the N atom to which they are attached, imidazolyl, O—C$_1$–C$_8$ alkyl, O-benzyl, O-phenyl and

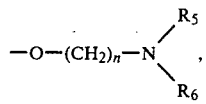

wherein n, $R_5$ and $R_6$ are defined as above; and wherein $R_2$ further represents a member selected from the group consisting of

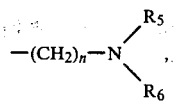

wherein n, $R_5$ and $R_6$ are defined as above, phenyl, tolyl, xylyl, and —SO$_2$—R$_7$, wherein $R_7$ is a straight or branched $C_1$–$C_{20}$ alkyl.

2. The compound of claim 1:
7-Pivaloxymethyl theophylline.
3. The compound of claim 1:
7-Hexanoyloxymethyl theophylline.
4. The compound of claim 1:
7-Butanoyloxymethyl theophylline.
5. The compound of claim 1:
7-(N,N-diethylamidosuccinyloxymethyl)theophylline.
6. The compound of claim 1:
7-(N,N-dimethylglycyloxymethyl)theophylline.
7. The compound of claim 1:
7-(α-Acetyloxyethylidene)theophylline.
8. The compound of claim 1:
7-(α-Butanoyloxyethylidene)theophylline.
9. The compound of claim 1:
7-α-Pivalyloxyethylidene)theophylline.
10. The compound of claim 1:
7-(αButanoyloxybenzyl)theophylline.
11. The compound of claim 1:
7-(Butanoyloxymethyl-1-methyl-3-isobutylxanthine.
12. The compound of claim 1:
7-Pivalyloxymethyl-1-methyl-3-isobutylxanthine.
13. The compound of claim 1:
7-Hexanoyloxymethyl-1-methyl-3-isobutylxanthine.
14. The compound of claim 1:
7-(N,N-Dimethylglycyloxymethyl)-1-methyl-3-isobutylxanthine.
15. The compound of claim 1:
7-(α-Butanoyloxyethylidene)-1-methyl-3-isobutylxanthine.
16. The compound of claim 1:
7-(α-Butanoyloxybenzyl)-1-methyl-3-isobutylxanthine.
17. The compound as defined by claim 1, wherein X is —O—.
18. The compound as defined by claim 1, wherein X is —S—.
19. The compound as defined by claim 1, wherein X is

20. The compound as defined by claims 17 or 18, wherein $R_1$ is H.
21. The compound as defined by claim 17 or 18, wherein $R_1$ is $C_1$–$C_7$ straight or branched alkyl.
22. The compound as defined by claim 17, wherein $R_1$ is CCl$_3$.
23. The compound as defined by claim 17, wherein $R_1$ is CBr$_3$.
24. The compound as defined by claim 17, wherein $R_1$ is CI$_3$.
25. The compound as defined by claim 17, wherein $R_1$ is

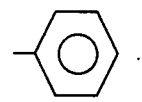

26. The compound as defined by claim 17, wherein $R_2$ is

and $R_4$ is $C_2$–$C_{20}$ straight or branched alkyl.
27. The compound as defined by claim 17, wherein $R_2$ is

and $R_4$ is cyclo ($C_3$–$C_{10}$) alkyl.
28. The compound as defined by claim 17, wherein $R_2$ is

and $R_4$ is

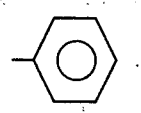

29. The compound as defined by claim 17, wherein $R_2$ is

and $R_4$ is

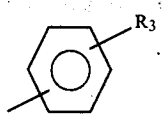

30. The compound as defined by claim 17, wherein $R_2$ is

and R$_4$ is

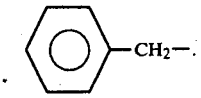

31. The compound as defined by claim 17, wherein R$_2$ is

and R$_4$ is

32. The compound as defined by claim 17, wherein R$_2$ is

and R$_4$ is

33. The compound as defined by claim 17, wherein R$_2$ is

and R$_4$ is

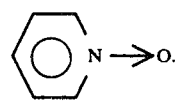

34. The compound as defined by claim 17, wherein R$_2$ is

and R$_4$ is

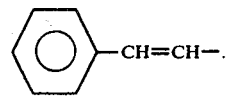

35. The compound as defined by claim 17, wherein R$_2$ is

and R$_4$ is the residue of any naturally occurring amino acid.

36. The compound as defined by claim 17, wherein R$_2$ is

and R$_4$ is the residue of any N-substituted amino acid.

37. The compound as defined by claim 17, wherein R$_2$ is

and R$_4$ is the residue of an N,N-C$_1$-C$_5$-dialkyl, cycloalkyl, N-heteroaromatic or N—C$_1$-C$_5$ alkyl aniline amino acid.

38. The compound as defined by claim 17, wherein R$_2$ is

and R$_4$ is

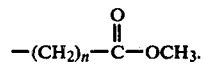

39. The compound as defined by claim 17, wherein R$_2$ is

and R$_4$ is

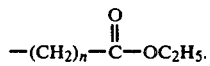

40. The compound as defined by claim 17, wherein R$_2$ is

and R$_4$ is $$-(CH_2)_n-\overset{\overset{O}{\|}}{C}-N\overset{R_5}{\underset{R_6}{\diagdown}}.$$

41. The compound as defined by claim 17, wherein $R_2$ is $$-\overset{\overset{O}{\|}}{C}-R_4$$

and $R_4$ is imidazolyl.

42. The compound as defined by claim 17, wherein $R_2$ is $$-\overset{\overset{O}{\|}}{C}-R_4$$

and $R_4$ is $O-C_1-C_8$ alkyl.

43. The compound as defined by claim 17, wherein $R_2$ is $$-\overset{\overset{O}{\|}}{C}-R_4$$

and $R_4$ is O-benzyl.

44. The compound as defined by claim 17, wherein $R_2$ is $$-\overset{\overset{O}{\|}}{C}-R_4$$

and $R_4$ is O-phenyl.

45. The compound as defined by claim 17, wherein $R_2$ is $$-\overset{\overset{O}{\|}}{C}-R_4$$

and $R_4$ is $$-O-(CH_2)_n-N\overset{R_5}{\underset{R_6}{\diagdown}}.$$

46. The compound as defined by claim 17, wherein $R_2$ is $$-(CH_2)_n-\overset{\overset{O}{\|}}{C}-N\overset{R_5}{\underset{R_6}{\diagdown}}.$$

47. The compound as defined by claim 17, wherein $R_2$ is phenyl.

48. The compound as defined by claim 17, wherein $R_2$ is tolyl.

49. The compound as defined by claim 17, wherein $R_2$ is xylyl.

50. The compound as defined by claim 17, wherein $R_2$ is $-SO_2-R_7$.

51. A method for the topical treatment of dermal inflammation on a warm-blooded animal afflicted with same which comprises topically applying to such dermal inflammation an anti-inflammatory effective amount of a compound having the structural formula (I)

wherein each R, which may be the same or different, represents a member selected from the group consisting of $-CH_3$, $-C_2H_5$, $-C_3H_7$, iso-$C_3H_7$, $-C_4H_9$, iso-$C_4H_9$, pentyl, benzyl, allyl, 2-hydroxyethyl, cyclohexyl, 2-isobutenyl, hydroxymethyl, 2-phenylethyl and $-CH_2O-R_2$, wherein $R_2$ is defined infra; wherein $R_1$ represents a member selected from the group consisting of H, $C_1-C_7$ straight or branched alkyl, $CCl_3$, $CBr_3$, $CI_3$, $CH_3O-CH_2-$, $(CH_3)_2NCH_2-$, $-CHO$, wherein $R_3$ represents a member selected from the group consisting of $-OH$, halogen, $-OCH_3$, $-COOCH_3$, $-NO_2$ and $-OCOCH_3$; wherein X is $-O-$, $-S-$, or $$-\overset{\overset{R_1}{|}}{N}-;$$

and wherein $R_2$ represents a member selected from the group consisting of $$-\overset{\overset{O}{\|}}{C}-R_4,$$

wherein $R_4$ is a member selected from the group consisting of $C_2-C_{20}$ straight or branched alkyl, cyclo($C_3-C_{10}$)alkyl,

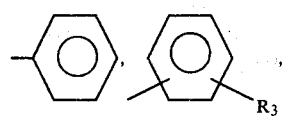

wherein R₃ is defined as above,

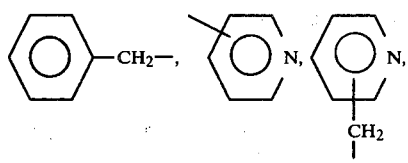

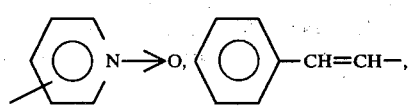

the residue of any naturally occurring amino acid, the residue of any N- substituted amino acid, wherein said substituent is any amino acid protective group cleavable via hydrogenolysis or hydrolysis, the residue of an N,N-$C_1$-$C_5$-dialkyl, cycloalkyl, N-heteroaromatic or N—C-$_1$-$C_5$ alkyl aniline amino acid,

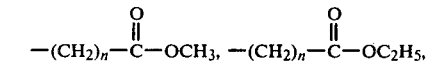

wherein n represents an integer of from 1–5 and $R_5$ and $R_6$ which may be the same or different represent $C_1$-$C_5$ alkyl or together form a heterocyclic ring with the N atom to which they are attached, imidazolyl, O—C-$_1$-$C_8$ alkyl, O-benzyl, O-phenyl and

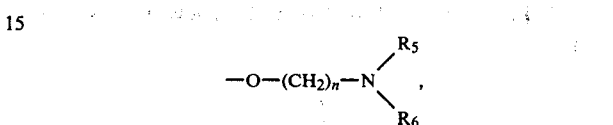

wherein n, $R_5$ and $R_6$ are defined as above; and wherein $R_2$ further represents a member selected from the group consisting of straight or branched $C_1$-$C_{20}$ alkyl,

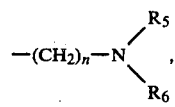

wherein n, $R_5$ and $R_6$ are defined as above, phenyl, tolyl, xylyl, and -$SO_2$-$R_7$, wherein $R_7$ is a straight or branched $C_1$-$C_{20}$ alkyl.

* * * * *